US006253710B1

(12) United States Patent
Ward et al.

(10) Patent No.: US 6,253,710 B1
(45) Date of Patent: Jul. 3, 2001

(54) ODOR CONTROL FOR ANIMAL LITTER

(75) Inventors: Kevin A. Ward, Dublin, OH (US); Jamie Bohn, Shawnee, OK (US)

(73) Assignee: The Sherwin-Williams Company, Cleveland, OH (US)

( * ) Notice: Subject to any disclaimer, the term of this patent is extended or adjusted under 35 U.S.C. 154(b) by 0 days.

(21) Appl. No.: 09/344,146

(22) Filed: Jun. 24, 1999

Related U.S. Application Data

(60) Provisional application No. 60/090,545, filed on Jun. 24, 1998.

(51) Int. Cl.⁷ .................................................. A01K 29/00
(52) U.S. Cl. ............................................................ 119/171
(58) Field of Search ................................. 119/171, 172, 119/173; 424/45, 76.5, 76.6, 76.7

(56) References Cited

U.S. PATENT DOCUMENTS

| | | | |
|---|---|---|---|
| 3,675,625 | * 7/1972 | Miller et al. | 119/173 |
| 3,735,734 | * 5/1973 | Pierce, III et al. | 119/173 |
| 3,892,846 | * 7/1975 | Wortham | 424/76.6 |
| 3,921,581 | * 11/1975 | Brewer | 119/173 |
| 3,983,842 | * 10/1976 | Marion et al. | 119/171 |
| 4,078,050 | 3/1978 | Hart | 424/76 |
| 4,085,704 | * 4/1978 | Frazier | 119/173 |
| 4,154,817 | * 5/1979 | Tsuchiya et al. | 424/76.6 |
| 4,203,388 | 5/1980 | Cortigene et al. . | |
| 4,405,354 | 9/1983 | Thomas, II et al. | 71/21 |
| 4,494,482 | * 1/1985 | Arnold | 119/173 |
| 4,517,919 | * 5/1985 | Benjamin et al. | 119/173 |
| 4,649,862 | 3/1987 | Neary . | |
| 4,840,792 | 6/1989 | Joulain et al. | 424/76.1 |
| 4,852,518 | 8/1989 | Yananton . | |
| 4,949,672 | 8/1990 | Ratcliff et al. . | |
| 4,957,063 | * 9/1990 | Heitfeld et al. | 119/172 |
| 5,016,568 | * 5/1991 | Stanislowski et al. | 119/173 |
| 5,094,190 | 3/1992 | Ratcliff et al. | 119/173 |
| 5,097,799 | 3/1992 | Heitfeld et al. | 119/172 |
| 5,135,743 | * 8/1992 | Stanislowski et al. | 424/76.6 |
| 5,152,250 | * 10/1992 | Loeb | 119/171 |
| 5,176,879 | 1/1993 | White et al. | 422/5 |
| 5,183,655 | 2/1993 | Stanislowski et al. | 424/76.6 |
| 5,189,987 | 3/1993 | Stanislowski et al. | 119/171 |
| 5,295,456 | * 3/1994 | Lawson | 119/172 |
| 5,935,554 | * 8/1999 | Tomlinson | 424/45 |
| 5,945,085 | * 8/1999 | Salas et al. | 424/45 |
| 5,970,915 | * 10/1999 | Schlueter et al. | 119/171 |

FOREIGN PATENT DOCUMENTS

| | | | | |
|---|---|---|---|---|
| 0 109 275 A2 | 11/1983 | (EP) | | A01K/1/015 |
| 0 201 209 A2 | 4/1986 | (EP) | | A61L/9/01 |
| 0 247 946 A1 | 5/1987 | (EP) | | A61L/9/01 |
| 2 629 678 A1 | 4/1988 | (FR) | | A01K/1/15 |
| WO 81/02891 A1 | 10/1981 | (WO) | | C05F/3/04 |
| WO 96/04940 A1 | 2/1996 | (WO) | | A61L/9/01 |
| WO 96/08425 A2 | 3/1996 | (WO) | | B65D/83/14 |

* cited by examiner

*Primary Examiner*—Charles T. Jordan
*Assistant Examiner*—Yvonne R. Abbott
(74) *Attorney, Agent, or Firm*—Vivien Y. Tsang; Robert E. McDonald; Paul R. Katterle

(57) ABSTRACT

This invention relates to an odor control liquid and aerosolized composition for deodorizing and controlling odor of animal wastes by contact therewith, comprising a non-aqueous volatile carrier and an odor control agent. The liquid and aerosolized composition can be applied in liquid form directly to the animal litter and/or the animal container and/or the animal waste. A related object of this invention is to provide a method for preventing sticking and contamination on the surfaces of a litter container, comprising applying to the container an effective amount of a powdered release agent or powdered odor control agent in a non-aqueous volatile carrier.

26 Claims, No Drawings

ODOR CONTROL FOR ANIMAL LITTER

This application claim to provisional application 60/090,545 Jun. 24, 1998.

Animal litter odors have been dealt with by the use of deodorizers. U.S. Pat. No. 4,203,388 to Cortigene et al. teaches the use of a deodorant such as sodium bicarbonate, in amounts of between about 1% and about 10% of the dry weight of the litter. Such large amounts of deodorizer are necessitated since the litter itself is also used as an absorbent for urine, requiring the deodorizer to be homogeneously dispersed throughout the particles of the litter.

U.S. Pat. No. 3,675,625 to Miller et al, teaches a litter which is "activated" by heating and then contacted with an odor control agent, such as pine oil, citrus oil, camphor or the like.

U.S. Pat. No. 5,094,190 to Ratcliff et al teaches an odor control animal litter to which a boron-containing liquid material has been applied. Further, U.S. Pat. No. 5,183,655 teaches an odor control animal litter that has applied to it an effective amount of pine oil in combination with an effective amount of boric acid. In U.S. Pat. No. 5,097,799, odor control agents selected from the group consisting of guanidine salts, alkali metal fluorides, alkali metal bisulfites, and mixtures thereof, are applied to the litter using an aqueous dispersion to produce an odor control animal litter.

The prior art also discloses attempts to prevent the formation of certain unpleasant odors. For example, U.S. Pat. No. 4,405,354 to Thomas et al. discloses the use of buffering agents to prevent gaseous ammonia from escaping into the air. However, such buffering agents serve only to prevent the formation of gaseous ammonia, doing nothing against other unpleasant odors. Further, the amounts of such agents range from about 0.5% to about 25% by weight, since all of the absorbent litter must be treated with the agent to provide sufficient contact with the urine.

Fungicides and bacteriostats have also been disclosed in the prior art as means to prevent the formation of odors in animal litters. U.S. Pat. No. 4,517,919 to Benjamin et al. discloses the use of undecylenic acid in amounts from about 1000 to about 10,000 ppm and a bacteriostat in amounts from about 25 to 500 ppm.

Still other prior art methods for preventing odor development from bacterial action have included heating to destroy bacteria, and desiccation of the litter by heat or evaporation. U.S. Pat. No. 4,649,862 to Neary discloses a sanitizing device for the litter box which applies heat to the litter to destroy bacteria.

Another known prior art odor abatement system employs a litter box liner which acts in conjunction with the litter. U.S. Pat. No. 4,852,518 to Yananton teaches the use of a sorptive-desiccant pad structure to prevent significant odor formation. The patent teaches that the pad disperses and evaporates the urine, causing bacteria to die or become dormant, and thereby preventing odor formation. Non-absorbent litter is employed to aid liquid transfer to the pad.

U.S. Pat. No. 4,494,482 to Arnold also discloses the use of an absorbent pad to prevent odor formation. This patent further teaches the use of about 5000 to about 30,000 pm of a bacteriostat in the absorbent pad to control odor. Because these pads are used in conjunction with absorbent litter, e.g., clay, the suggested amounts of bacteriostat in the pad are extremely high to account for the large amount of untreated litter in the litter box. According the patent's teachings, a pad weighing 50 grams used in conjunction with 2000 grams of untreated clay must contain 4100 pm of bacteriostat in order to maintain an overall level of 100 pm of bacteriostat in the combined material in the litter box.

None of the prior art references teach or suggest the use of a liquid or aerosolized odor control composition that may be sprayed onto animal litter and animal litter containers, to reduce odor and extend the useful life of litter. Furthermore, none of the prior art has taught the combination of an odor control agent in combination with an antibacterial agent in a non-aqueous volatile carrier, to provide long-term odor control for animal litters.

SUMMARY OF THE INVENTION

It is an object of this invention to provide an odor control liquid and aerosolized composition for deodorizing and controlling odor of animal wastes by contact therewith, comprising a non-aqueous volatile carrier and an odor control agent.

It is another object of this invention to provide an odor control liquid and aerosolized composition for deodorizing and controlling odor of animal wastes by contact therewith, comprising a non-aqueous volatile carrier, an odor control agent, and an antibacterial agent.

It is yet another object of this invention to provide an odor control liquid and aerosolized composition for deodorizing and controlling odor of animal wastes by contact therewith, comprising a non-aqueous volatile carrier, an odor control agent, an antibacterial agent, and a powdered release agent.

Still, another object of this invention is to provide an odor control animal litter comprising particles of an absorbent or adsorbent litter substrate, said particles being contacted with a liquid composition comprising an effective amount of an odor control composition comprising an odor control agent in a non-aqueous volatile carrier.

Yet still, another object of this invention is to provide a method for deodorizing and controlling odor of animal wastes in animal litter and animal litter containers, comprising applying directly to said litter or litter container a nonaqueous liquid composition comprising an odor control agent.

A related object of this invention is to provide a method for preventing sticking and contamination on the surfaces of a litter container, comprising applying to the container an effective amount of a powdered release agent or powdered odor control agent in a non-aqueous volatile carrier.

DESCRIPTION OF THE INVENTION

The odor control composition of this invention utilizes an odor control agent in a non-aqueous volatile carrier. According to this invention, an odor control agent can be any compound(s) that function(s) to mask odorous material, or any compound that reacts with odor-causing material to form non-odorous compounds. The odor control agent can be in a solid or liquid form. Some examples of odor control agents can be an acrylic ester such as lauryl methacrylate, (sold under trade name METAZENE by Pestco Company), sodium bicarbonate, benzalkonium chloride, bisulfite complexes of aldehydes and ketones, boric acid, borax, menthol, camphor, sodium bisulfate, lemon oil, and pine oil. Odor control agents can also be a powdered compounds such as magnesium silicates (talc), inorganic silicone and magnesium powders, sodium bicarbonate, chlorophyll, sodium dihydrogen phosphate, potassium acid phthalates, or other powdered odor control agents known to those skilled in the art, or mixtures thereof, which compounds also act as release agents. When the odor control agent is an acrylic ester, such as lauryl methacrylate, for example, the concentration of the acrylic ester component can vary from about 1% by weight to about 70% by weight, preferably from about 1% to about 7% by weight, and most preferably from about 1% to about 3.5% by weight, of the total composition. Those skilled in the art will adjust the compositional levels of the odor control agent to ensure effective odor control and cost effectiveness.

In another embodiment of this invention, the odor control composition further comprises from about 0.01% to about 20% by weight of an antibacterial agent. Effective odor prevention for longer periods of time can be obtained with the use of an antibacterial agent added to the composition. Antibacterial agents can act to prevent the buildup of microorganisms that can develop over time, and may also act as a preservative for long term storage of the liquid composition. Although any broad spectrum antibacterial agent is suitable for use herein, preferred antibacterial agents are the halogenated aromatic hydrocarbons. Suitable examples are p-chloro-m-cresol, hexachlorophene, 2,4,4'-trichloro-2'-hydroxydiphenyl ether (also known as Triclosan, commercially available under the tradename MICROBAN from Clinitex Corporation, trichlorocarbanilide, 2,4-dichloro-m-xylenol, 3,4,5-tribromosalicylanilide, 3,5,3',4'-tetrachlorosalicylanilide, 3,5,3',5'-tetrachlorodiphenyl sulfide, and mixtures thereof. Due to the effectiveness of these antibacterial agents, these materials can be used at very low levels that an effective product can be obtained without the high cost or toxicity being significant factors of consideration. The antibacterial agent is preferably present at from about 0.01% by weight to 20% by weight of the total composition, and more preferably, at from about 0.3% to about 10% by weight, of the total composition.

In yet another embodiment of this invention, the odor control composition can further comprise a powdered release agent. Release agents such as magnesium silicates (talc) can be defined as a compound that can provide benefits of stick prevention, contamination prevention, and quicker drying time, visual indication of coverage, as well as provide a coating or physical barrier to odorous compounds on porous materials. More preferably, the release agent will also be an odor absorbing powder such as, for example, inorganic silicone and magnesium powders, sodium bicarbonate, chlorophyll, sodium dihydrogen phosphate, potassium acid phthalates, or mixtures thereof. The powdered release agent can be present at about 0.1% by weight to about 10% by weight of the total composition.

The non-aqueous volatile carrier of this invention should have a volatility greater than water. Preferably, the nonaqueous volatile carrier is acetone, which when sprayed on a substrate, will dry most quickly and not have the potential problems of clumping if sprayed onto absorbent or adsorbent particulate materials. Another preferable non-aqueous volatile carrier is isopropanol. Optionally, a fragrance may be added to the composition. Representative examples of fragrance components generally include, but are not limited to: volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinold and opoponax resinold); "synthetic" oils such as Bergamot 37 and 430, Geranium 76 and Pomeransol 314, and Powder Mask CE-32907); aldehydes and ketones (such as beta-methyl naphthyl ketone, p-tert-butyl-a-methyl hydrocinnamic aldehyde and p-tert-amyl cyclohexanone); polycyclic compounds (such as Coumarin and beta-naphthyl methyl ether); esters (such as diethyl phthalate, phenylethyl phenylacetate). Fragrances also include esters and essential oils derived from floral materials and fruits, citrus oils, absolutes, aldehydes, etc. and alcohols (such as dimyrcetol, phenylethyl alcohol and tetrahydromuguol).

Thus, the odor control compositions of this invention can be used as a premixed litter container additive for domesticated animals and pets to effectively eliminate and prevent the development of unpleasant odors in animal litter containers for extended periods of time. The odor control composition can be applied directly to the litter container, or directly to particles of an absorbent or adsorbent litter substrate, and/or directly to the litter container. Any absorbent or adsorbent litter substrate material that is commercially available can be contacted with the odor control composition of this invention. Some examples of absorbent litter substrates include minerals, typically clay such as kaolinites, montmorillonites, or bentonites; fly ash as obtained from the burning of coal; pelletized absorbent materials (e.g. sawdust or polyurethane foam); and the like. In addition to being used in animal litter containers, the compositions can be used in many environments, including animal containment areas, living areas, production areas, work areas and automobiles, for example.

To produce an odor control animal litter, the odor control composition of this invention is applied directly to the absorbent or adsorbent litter substrate in an effective amount. For litter containers, it is most preferred that powdered release agents such as talc are used. In this respect, the talc acts not only as a stick preventive, but also coats the surface and fills the pores of the litter container, thereby forming a physical barrier to the prevent contamination and/or absorption of odorous materials.

An odor control composition of this invention can be made as follows: To a batch tank, add 66.1 weight percent acetone and begin high speed agitation to form a vortex in the acetone. Add 0.3 weight percent 2-hydroxy-2',4,4'-trichlorodiphenyl ether and magnesium silicate talc into the vortex, which results in a milky white solution. Add 3.5 weight percent of lauryl methacrylate, and optionally 0.1 weight percent of Powder Mask fragrance (CE-32907) to the center of the vortex. Close the batch lid and continue mixing at a high speed for 10 minutes, then reduce mixing to a moderate mixing speed. Maintain a moderate mixing speed during filling to ensure that the talc stays suspended in the acetone. The liquid compositions of this invention can be adapted for discharge from a pressurized container to form an aerosol spray. When formulated as an aerosol spray, propellants such as propane, butane, or other known propellants, can be used.

The odor control composition is preferably applied in the form of a liquid, or as an aerosol spray. An aerosol composition generally means an odor control liquid composition adapted for discharge from a pressurized container to form an aerosol spray. According to this invention, the aerosol composition comprises a non-aqueous volatile carrier, an odor control agent, and a propellant. "Applying" the odor control composition in this invention means wetting at least a significant portion of the surface area of the solid absorbent or adsorbent material and/or container therefor, with the odor control composition, which could include spraying, soaking, or impregnating. The liquid or aerosol composition can be applied directly to the litter or litter container. When applied in either the liquid or aerosolized form, a mist of wet film is applied, whereafter the solvent quickly evaporates for fast drying. When the odor control composition is applied in aerosolized form, an even distribution of the odor control agent can be achieved over the desired area. Preferably, when the liquid odor control composition comprising a an odor control agent, a powdered release agent, and a non-aqueous volatile carrier is sprayed onto a porous litter container, sticking and contamination of the container and litter can be prevented. More preferably, the liquid composition comprises an odor control agent and a powdered release agent in a nonaqueous carrier, adapted for discharge from a pressurized container to form an aerosol spray. Aerosol application of the composition of this invention is advantageous for several reasons, such as: (1) because an aerosol droplet is typically a small particle size (typically 5–30 micron in diameter), a fine mist can be applied with an even distribution on the applied surfaces; (2) after application, the small droplets have a much faster drying time; (3) a large number of particles are released every second, providing a greater likelihood of impacting the odor molecules; and (4) high likelihood of absorption into a porous substrate or surface; to name a few. Economically, due to the ability to perform an efficient application with an aerosol spray, the cost of the product is less and product waste is minimized, compared to typical dry powder applications. Compositions comprising the powdered release agent can be easily seen for proper application, and easily removable at the time of cleaning. Aerosol application also allows for a more even distribution of the odor control agent over applied areas, The amount of the odor control composition applied should be sufficient to effectively eliminate or control the odor, and at the same time, not be toxic or harmful to the environment or animal occupants.

We claim:

1. An odor control animal litter comprising: particles of an absorbent or an adsorbent litter substrate, said particles being contacted with a liquid composition comprising an effective amount of an odor control composition comprising an odor control agent in a non-aqueous volatile carrier and a release agent, wherein the release agent can be selected from the group consisting of talc, inorganic silicone and magnesium powders, sodium bicarbonate, chlorophyll, sodium dihydrogen phosphate, potassium acid phthalates, or mixtures thereof.

2. An odor control animal litter comprising: particles of an absorbent or an adsorbent litter substrate, said particles being contacted with a liquid composition comprising an effective amount of an odor control composition comprising an odor control agent in a non-aqueous volatile carrier, wherein the odor control agent is lauryl methacrylate and the non-aqueous volatile carrier is acetone.

3. An odor control liquid composition for deodorizing and controlling odor of animal wastes by contact therewith, comprising
   a) a non-aqueous volatile carrier,
   b) an odor control agent; and
   c) an antibacterial agent; and
   d) a release agent, wherein the release agent is an odor absorbing powder.

4. The composition of claim 3, wherein the release agent can be selected from the group consisting of talc, inorganic silicone and magnesium powders, sodium bicarbonate, chlorophyll, sodium dihydrogen phosphate, potassium acid phthalates, or mixtures thereof.

5. An odor control liquid composition for deodorizing and controlling odor of animal wastes by contact therewith, comprising
   a) a non-aqueous volatile carrier;
   b) an odor control agent; and
   c) an antibacterial agent; wherein the odor control agent is lauryl methacrylate, the non-aqueous volatile carrier is acetone, and the antibacterial agent is 2-hydroxy-2',4,4'-trichlorodiphenyl ether.

6. An odor control liquid composition for deodorizing and controlling odor of animal wastes by contact therewith, comprising:
   a) a non-aqueous volatile carrier;
   an odor control agent;
   c) an antibacterial agent; and
   d) a release agent, wherein the release agent is an odor absorbing powder.

7. The composition of claim 6, wherein the release agent can be selected from the group consisting of talc, inorganic silicone and magnesium powders, sodium bicarbonate, chlorophyll, sodium dihydrogen phosphate, potassium acid phthalates, or mixtures thereof.

8. The composition of claim 6, wherein the odor control agent is lauryl methacrylate, the non-aqueous volatile carrier is acetone, the antibacterial agent is 2-hydroxy-2',4,4'-trichlorodiphenyl ether, and the release agent is talc.

9. The composition of claim 6, further comprising a fragrance.

10. A method for deodorizing and controlling odor of animal wastes in animal litter containers, comprising applying directly to said litter container a nonaqueous liquid composition which comprises an odor control agent in a nonaqueous volatile carrier; wherein the odor control agent is lauryl methacrylate and the non-aqueous volatile carrier is acetone.

11. The method of claim 10, wherein the non-aqueous liquid composition further comprises an antibacterial agent.

12. The method of claim 11, wherein the antibacterial agent can be selected from the group consisting of 2-hydroxy-2',4,4'-trichlorodiphenyl ether, p-chloro-m-cresol, hexachlorophane, trichlorocarbanilide, 2,4-dichloro-m-xylenol, 3,4,5-tribromosalicylanilide, 3,5,3',4'-tetrachlorosalicylanilide, 3,5,3',5'-tetrachlorodiphenyl sulfide, and mixtures thereof.

13. A method for deodorizing and controlling odor of animal wastes in animal litter, comprising applying directly to said litter a non-aqueous liquid composition which comprises an odor control agent in a non-aqueous volatile carrier and a release agent; wherein the release agent is an odor absorbing powder.

14. The method of claim 13, wherein the release agent can be selected from the group consisting of talc, inorganic silicone and magnesium powders, sodium bicarbonate, chlorophyll, sodium dihydrogen phosphate, potassium acid phthalates, or mixtures thereof.

15. The method of claim 13, wherein the release agent is talc.

16. An odor control liquid composition for deodorizing and controlling odor of animal wastes by contact therewith and adapted for discharge from a pressurized container to thereby form an aerosol spray comprising:
   a) a non-aqueous volatile carrier;
   b) an odor control agent;
   c) a propellant; and
   d) a release agent.

17. The composition of claim 16, further comprising an antibacterial agent.

18. The composition of claim 17, wherein the antibacterial agent can be selected from the group consisting of 2-hydroxy-2',4,4'-trichlorodiphenyl ether, p-chloro-m-cresol, hexachlorophane, trichlorocarbanilide, 2,4-dichloro-m-xylenol, 3,4,5-tribromosalicylanilide, 3,5,3',4'-tetrachlorosalicylanilide, 3,5,3',5'-tetrachlorodiphenyl sulfide, and mixtures thereof.

19. The composition of claim 16, wherein the release agent is an odor absorbing powder.

20. The composition of claim 16, wherein the release agent can be selected from the group consisting of talc, inorganic silicone and magnesium powders, sodium bicarbonate, chlorophyll, sodium dihydrogen phosphate, potassium acid phthalates, or mixtures thereof.

21. A method of preventing contamination of the surfaces of an animal litter container, comprising applying directly to said container a non-aqueous liquid composition which comprises an odor control agent in a non-aqueous volatile carrier, and a powdered release agent.

22. The method of claim 21, wherein the powdered release agent can be selected from the group consisting of talc, inorganic silicone and magnesium powders, sodium bicarbonate, chlorophyll, sodium dihydrogen phosphate, potassium acid phthalates, or mixtures thereof.

23. The odor control liquid composition of claim 21, wherein the powdered release agent can be selected from the group consisting of talc, inorganic silicone and magnesium powders, sodium bicarbonate, chlorophyll, sodium dihydrogen phosphate, potassium acid phthalates, or mixtures thereof.

24. A method of preventing sticking to litter containers, comprising: applying to said container a non-aqueous liquid composition which comprises an odor control agent in a non-aqueous volatile carrier, and a powdered release agent.

25. The method of claim 24, wherein the powdered release agent can be selected from the group consisting of talc, inorganic silicone and magnesium powders, sodium bicarbonate, chlorophyll, sodium dihydrogen phosphate, potassium acid phthalates, or mixtures thereof.

26. The method of claim 24, wherein the liquid composition is applied in aerosol form.

* * * * *